United States Patent
Duncan et al.

(10) Patent No.: US 11,622,987 B2
(45) Date of Patent: Apr. 11, 2023

(54) AQUEOUS EXTRACTION PROCESS OF PLANTS, METHOD THEREOF, AND PRODUCT BY PROCESS

(71) Applicant: Eir Pharmaceuticals, LLC, Olathe, KS (US)

(72) Inventors: William P. Duncan, Olathe, KS (US); Lauren S. Gollahon, Lubbock, TX (US); William C. Putnam, Frisco, TX (US)

(73) Assignee: EIR Pharmaceuticals, LLC, Olathe, KS (US)

( * ) Notice: Subject to any disclaimer, the term of this patent is extended or adjusted under 35 U.S.C. 154(b) by 0 days.

(21) Appl. No.: 16/590,807

(22) Filed: Oct. 2, 2019

(65) Prior Publication Data
US 2020/0101126 A1  Apr. 2, 2020

Related U.S. Application Data

(60) Provisional application No. 62/740,047, filed on Oct. 2, 2018.

(51) Int. Cl.
| | |
|---|---|
| A61K 36/00 | (2006.01) |
| A61K 36/54 | (2006.01) |
| A61K 9/00 | (2006.01) |
| A61K 36/28 | (2006.01) |
| A61K 36/53 | (2006.01) |
| A61K 36/254 | (2006.01) |
| A61K 36/31 | (2006.01) |
| A61K 36/481 | (2006.01) |
| A61K 36/8998 | (2006.01) |
| A61K 36/355 | (2006.01) |

(52) U.S. Cl.
CPC ............ *A61K 36/54* (2013.01); *A61K 9/0014* (2013.01); *A61K 9/0019* (2013.01); *A61K 9/0053* (2013.01); *A61K 36/254* (2013.01); *A61K 36/28* (2013.01); *A61K 36/31* (2013.01); *A61K 36/355* (2013.01); *A61K 36/481* (2013.01); *A61K 36/53* (2013.01); *A61K 36/8998* (2013.01); *A61K 2236/37* (2013.01); *A61K 2236/39* (2013.01); *A61K 2236/53* (2013.01)

(58) Field of Classification Search
None
See application file for complete search history.

*Primary Examiner* — Russell G Fiebig
(74) *Attorney, Agent, or Firm* — Law Office of Mark Brown, LLC; Christopher M. DeBacker

(57) ABSTRACT

The preparation of an aqueous extract resulting from an aqueous extraction process of *Cinnamomum aromaticum, Arctium lappa, Viticis fructus, Lonicera japonica, Acanthopanax gracilistylis, Raphanus sativus, Astragalus membranaceus* and *Hordeum vulgare* and the chemical composition comprising said extract or fraction thereof, and the use of said composition or fraction thereof for treating or preventing cancers and inflammation related diseases, hair loss, stimulating hair growth, increasing energy production, and boosting immunity.

15 Claims, 11 Drawing Sheets

Top Upstream Regulators

Upstream Regulators

| Name | p-value | Predicted Activation |
|---|---|---|
| HGF | 1.99E-13 | Inhibited |
| NUPR1 | 4.63E-13 | Activated |
| Vegf | 2.71E-12 | Inhibited |
| TP53 | 1.64E-09 | Activated |
| E2F4 | 1.93E-09 | |

Causal Network

| Name | p-value | Predicted Activation |
|---|---|---|
| HSPG2 | 1.59E-13 | Inhibited |
| NUPR1 | 3.11E-13 | Activated |
| axitinib | 4.29E-13 | Activated |
| Vegf | 7.94E-13 | Inhibited |
| HGF | 2.73E-12 | Inhibited |

FIG. 10

These top networks reveal that cancer cell metabolism (energy production) and proliferation are significantly affected by treatment with H.2. This effect could be amplified or inhibited based on the genes (molecules) involved.

AQUEOUS EXTRACTION PROCESS OF PLANTS, METHOD THEREOF, AND PRODUCT BY PROCESS

CROSS-REFERENCE TO RELATED APPLICATION

This application claims priority in U.S. Provisional Patent Application No. 62/740,047 Filed Oct. 2, 2018, which is incorporated herein by reference.

BACKGROUND OF THE INVENTION

1. Field of the Invention

The present invention relates generally to an aqueous extraction process and method for use thereof, and more specifically to an aqueous extraction process of specific plants for the chemical composition thereof.

2. Description of the Related Art

Existing methods for extracting key compounds or components for generating a chemical composition comprised of an extract thereof do exist. However, these processes have failed to adequately and reliably produce a chemical composition having the results of the present invention.

Heretofore there has not been available a system or method for an aqueous extraction process and resulting extract with the advantages and features of the present invention.

BRIEF SUMMARY OF THE INVENTION

The present invention generally provides for the preparation of an aqueous extract resulting from an aqueous extraction of individual or mixtures of *Cinnamomum cassia, Arctium lappa, Vitex agnus castus, Lonicera japonica, Acanthopanax gracilistylis, Raphanus sativus, Astragalus membranaceus* and *Hordeum vulgare* and the chemical composition comprising said extracts or fractions thereof, and the use of said compositions or fractions thereof for treating or preventing cancers and inflammation related diseases, hair loss, stimulating hair growth, increasing energy production, and boosting immunity.

The resulting extracts include a mixture of naturally occurring biologically active phytochemical compounds that possess a variety of beneficial animal and human health effects.

BRIEF DESCRIPTION OF THE DRAWINGS

The drawings constitute a part of this specification and include exemplary embodiments of the present invention illustrating various objects and features thereof.

FIG. 10 is a table including a summary of gene expression changes in the presence of an exemplary product of the extraction process (EPE001) using RNA-Seq analysis.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed manifestation.

Certain terminology will be used in the following description for convenience in reference only and will not be limiting. For example, up, down, front, back, right and left refer to the invention as orientated in the view being referred to which the referral is directed. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

Figure 1:
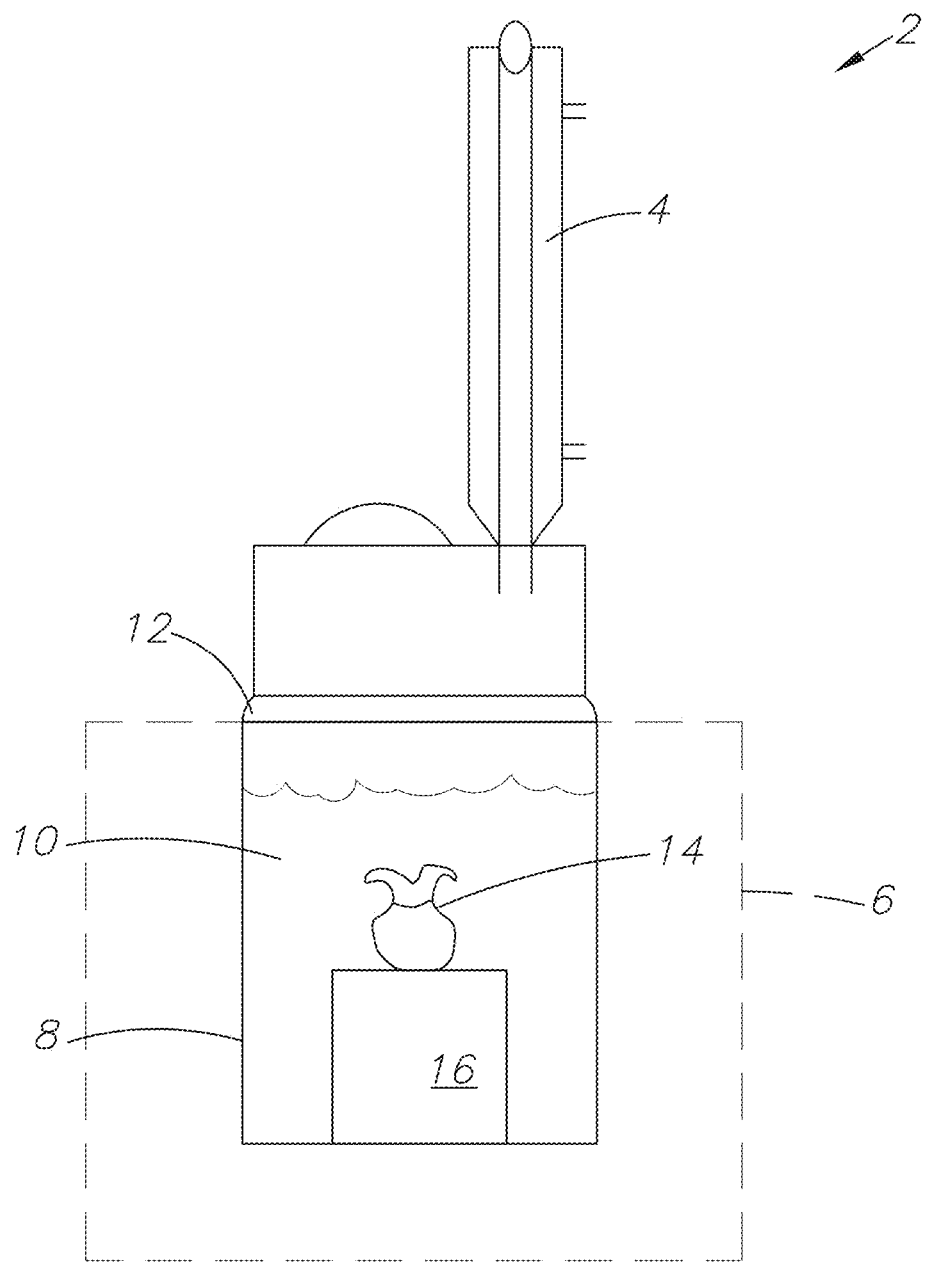
FIG. 1 is a diagram of a preferred embodiment static (batch) aqueous extraction system.

II. Preferred Embodiment Static (Batch) System and Aqueous Extraction Process FIG. 1 shows a static aqueous extraction system 2. A process utilizing this static system 2 results in a product capable of producing desired results as described in more detail and in specific examples below.

Individual or a desired mixture of *Cinnamomum cassia, Arctium lappa, Vitex agnus castus, Lonicera japonica, Acanthopanax gracilistylis, Raphanus sativus, Astragalus membranaceus* and *Hordeum vulgare* are combined in equal or various amounts by dry weight and placed in a spunbond nonwoven fabric container 14. The fabric container may be placed upon a pedestal 16 within the extraction apparatus 8 for optimal results. The spunbond nonwoven fabric container 14 is sealed and then fixed within the extraction apparatus 8 containing reverse-osmosis membrane filtered purified or distilled water 10 as shown in FIG. 1. The extraction apparatus may be made of a stainless steel or glass vessel. The extraction apparatus 8 is contained within a heating element 6. The extraction apparatus is closed and sealed with a seal 12 and then heated such that the water 10 is boiling for 3-6 hrs. Some of the vapor is discharged through the water-cooled condenser outlet 4 affixed to the top of the extraction apparatus 8 allowing some volatiles to escape while retaining a portion that are condensed and returned to the extraction apparatus. The seal retains the condenser unit 4 in connection with the extraction apparatus 8. The resulting extraction mixture is then filtered in succession using a membrane filter with a pore size not bigger than $10^{-6}$ m (1 micron) and purified water at 90-100° C., 70-85° C., 40-60° C., 15-30° C., and 5-15° C., providing the final product filtrate (extract) that contains ~370 mg of biologically active solid ingredients per liter of aqueous extract. Example compounds identified in the aqueous extract include acids such a chlorogenic and cinnamic acid, aldehydes, e.g. cinnamaldehyde and lignans, e.g. arctiin.

For example, by dry weight, for each liter of water, 220 mg of *Cinnamomum cassia*, 110 mg *Arctium lappa*, 220 mg *Vitex agnus castus*, 110 mg *Lonicera japonica*, 110 mg *Acanthopanax gracilistylis*, 110 mg *Raphanus sativus*, 110 mg *Astragalus membranaceus* and 220 mg *Hordeum vulgare* are combined and placed in a spunbond nonwoven fabric, and the spunbond nonwoven fabric sealed and then fixed within the extraction apparatus filled with reverse-osmosis membrane filter purified or distilled water. The extraction vessel is closed and then heated to boiling for 3 hrs. Some of vapor is discharged through the water-cooled condenser outlet affixed to the top of the extraction vessel allowing a portion of volatiles to escape while retaining some that are condensed and returned to the extraction vessel. The resulting hot extraction mixture, of these ingredients is referred to as, EPE001, from this point onward, is then filtered in succession via simple vacuum assisted filtration using membrane filters with a pore size not bigger than $10^{-6}$ m (1 micron) at 90-100° C., 70-85° C., 40-60° C., 15-30° C., and 5-15° C. providing the final product extract that contains ~370 mg of biologically active solid ingredients per liter of aqueous extract.

III. Alternative Embodiment Dynamic (Semi-Continuous Flow) System and Aqueous Extraction Process 52

Figure 2:
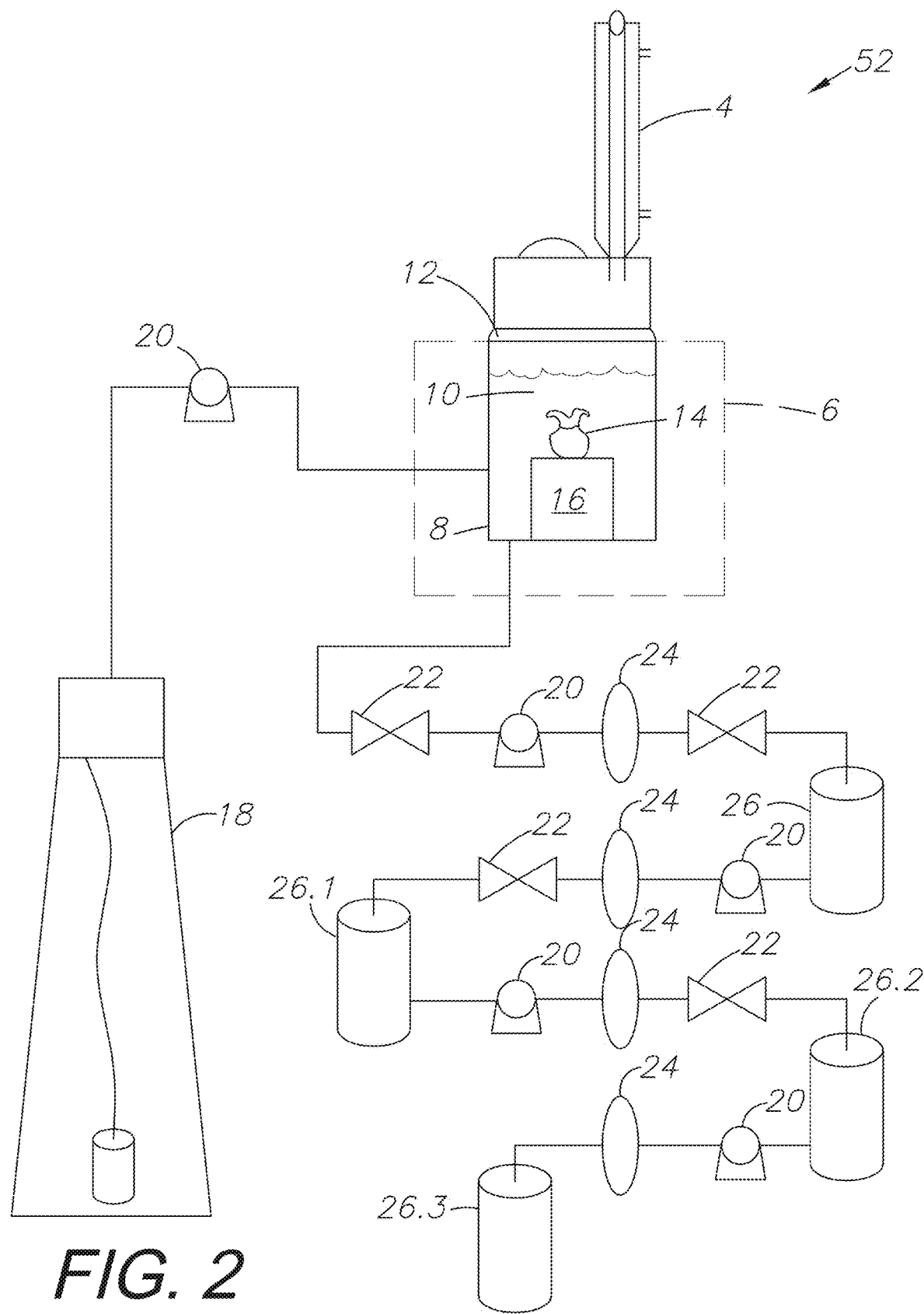
FIG. 2 is a diagram of an alternative embodiment dynamic (semi-continuous flow) aqueous extraction system.

FIG. 2 presents an alternative system for producing a chemical compound from an aqueous extraction process utilizing a dynamic system 52. In the same manner as the static system 2, an individual herb or a desired mixture of *Cinnamomum cassia, Arctium lappa, Vitex agnus castus, Lonicera japonica, Acanthopanax gracilistylis, Raphanus sativus, Astragalus membranaceus* and *Hordeum vulgare*, are combined in equal or various amounts by dry weight and placed in a spunbond nonwoven fabric container 14, and the spunbond nonwoven fabric container 14 is sealed and then fixed within the extraction vessel 8. Reverse-osmosis membrane filter purified, or distilled water 10 is then pumped into the extraction vessel 8 via a pump 20. The extraction apparatus 8 is contained within a heating element 6. The extraction apparatus is closed and sealed with a seal 12 and heated to boiling for 4-6 hrs. Some of the vapor is discharged through the water-cooled condenser outlet 4 affixed to the top of the extraction vessel allowing some volatiles to escape while retaining some that are condensed and returned to the extraction vessel. The resulting extraction mixture, EPE001, is then filtered in succession by pressure driven filtration using filters with a pore size not bigger than $10^{-6}$ m (1 micron) utilizing a system of appropriately connected pumps and valves that allow for efficient transfer of the purified water extract at 70-95° C., followed by filtering the extract using purified water at 70-95° C., 40-60° C., 15-30° C., and 5-15° C., providing the final product extract that contains ~350 mg of active solid ingredients per liter of aqueous extract. This extraction process allows for a dynamic semi-continuous flow production of biologically active extract by pausing the process, recharging the spunbond nonwoven fabric with selected amounts of dried herbs and initiating the process by pumping purified water 10 into the extraction vessel 8 and restarting the heating device.

This process is made dynamic through the use of a large vessel of purified water 18 which is pumped using a pump 20 into the extraction vessel 8. It is then pulled out of the extraction vessel 8 using a series of valves 22, filters 24, and pumps 20 as shown in FIG. 2 into one or more storage containers 26, 26.1, 26.2, 26.3. The system can be run dynamically until all storage containers are filled, and as soon as there is volume in one storage container as shown, the aqueous extraction can pass onto the next pump and filter set. Purified water can be pumped into the vessel 8 from the reservoir 18 through an inlet in the reservoir near the top of the vessel. After the boiling step is complete, the aqueous extract can be pumped out through an outlet near the bottom of the vessel and through a single or series of decreasing pore-size filters with the final filter being a 0.2 μm filter. The filtrate would then be dispensed into a collection vessel as a finished product for a number of various uses.

The use of the extract resulting from the aqueous extraction processes as described herein are varied. A first use of the extract would be as a potential cancer therapeutic. This would provide an application to a broad range of solid cancers (neoplasias) due to effects of the extract chemical composition on mitochondrial function in cancer cells (e.g. apoptosis, autophagy, and mitochondrial membrane potential changes) as well as changes in transcriptional activation (promote or inhibit) of key genes associated with cancer progression or suppression. The benefits include a reduction or elimination of side effects common in existing cancer therapeutics. The preparation of the extract as presented herein provides for the delivery of biologically active compounds topically or as an aqueous oral dose. It has a bioactivation and bioavailability increase upon digestion associated with changes in pH. It causes a decrease in the proliferation of cancer cells and an inhibition of genes related to cancer cell growth.

A second use of the extract as presented herein would be an anti-inflammatory therapeutic. It provides a reduction in reactive oxygen species formation in normal cells. It reduces production of inflammatory cytokines. It also provides increased mobility with concurrent decrease in joint pain.

A third use is as an energy supplement. The extract provides an increase in beta-oxidation utilizing fatty acids as a substrate for generation of ATP. It provides increased energy production (e.g. mitochondrial efficiency). It also provides a decrease in glucose dependency as a metabolic substrate, while also reducing inflammation as described above.

A fourth use is as a weight loss supplement. The extract has been shown to increase beta-oxidation utilizing fatty acids as a substrate for generation of ATP. and a decrease in glucose dependency as a metabolic substrate. The extract has also been shown to decrease glucose dependency as a metabolic substrate. These metabolic changes are expected to cause weight loss. The extract has also been shown to provide an inhibition of some known obesity related gene expression.

A fifth use is for its antiviral effectiveness due to increased potential cell membrane resistance and decreased replication capabilities against clinically relevant viral strains including HIV, Influenza Virus, West Nile Virus, Adenovirus, and Polymavirus.

A sixth use is for its antimicrobial effectiveness due to its effectiveness against pathogenic bacterial infections including, *Streptococcus* sp., *Staphylococcus* sp., and *Listeria* sp.

A seventh use is for dermatological stem cell activity, such as for use for hair growth or other uses against skin conditions such as atopic dermatitis, psoriasis, and eczema.

An eighth use is for boosting the immune system. Specifically, inducing pluripotent stem cells to replace depleted populations of T-cell lymphocytes. This population replenishment has direct positive benefits in the mechanism of action related to the second and third uses as described above.

IV. Examples and Results Utilizing a Product by Process of Static (Batch) System and Aqueous Extraction Process 2 or Dynamic (Semi-Continuous Flow) System and Aqueous Extraction Process 52

FIGS. 3-9 show several examples and results thereof utilizing a product produced by the processes described above. Other examples are not explicitly shown, but the results are described below. Typical treatments for cancer involve chemicals that are not only toxic to infected cells but also other surrounding cells, tissues and systems. Because of this there is a growing need and interest for utilizing natural products for treatment of a variety of human diseases and conditions. Using the herein described process, a reproducible, aqueous extract of a combination of plants has been shown to be toxic to human cultured cancer cells but does not harm healthy cells.

Figure 3:
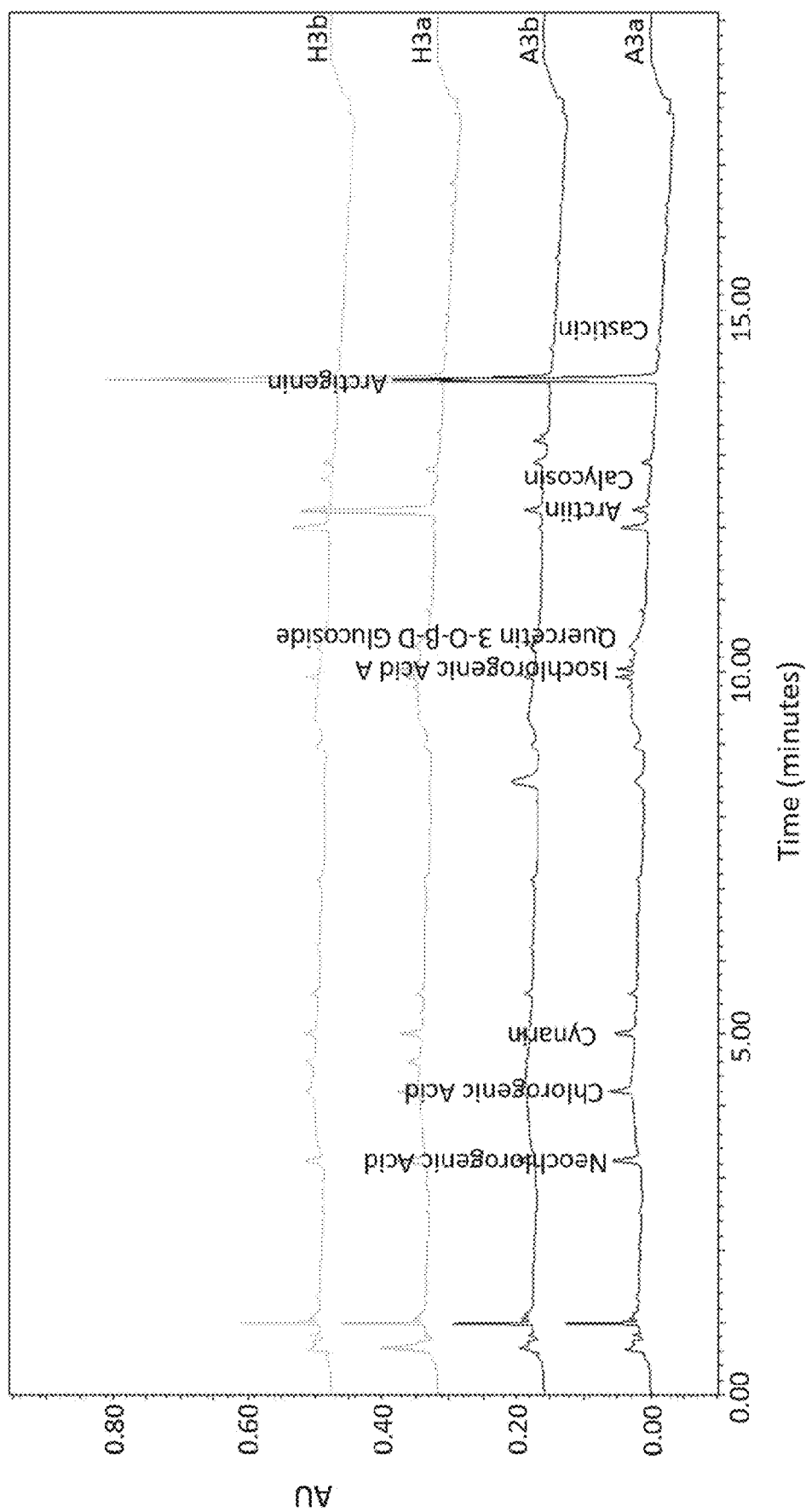
FIG. 3 is a LC-MS chromatogram depicting the components of an exemplary product (EPE001) of an extraction process utilizing one of the embodiments of the extraction systems of FIGS. 1 and 2.

In these examples, each of the eight herbs (*Cinnamomum cassia, Arctium lappa, Vitex agnus castus, Lonicera japonica, Acanthopanax gracilistylis, Raphanus sativus, Astragalus membranaceus* and *Hordeum vulgare*) were milled to a powder then passed through a 0.21 mm mesh sieve to exclude any large particulates. The powders were combined and placed into a spunbond nonwoven fabric bag and sealed then placed into a vessel containing reverse-osmosis purified water utilizing the static system 2 shown in FIG. 1 and alternatively the dynamic continuous system 52 shown in FIG. 2. After the vessel was sealed, the water was brought to a boil for 3 hours. The aqueous extract (EPE001) was split into four aliquots. Two aliquots were cooled to 80° C. before passing through either a qualitative filter (11 μm) or a 0.2 μm filter. The other two aliquots were allowed to cool to room temperature before being passed through either a qualitative filter (11 μm) or a 0.2 μm filter. A portion of each aliquot was lyophilized to dryness before being diluted with purified water to a final concentration of 3.6 mg extract residue per milliliter. Each of these samples were then utilized in analytical experimentation and bioassays to determine chemical composition and biological activity FIG. 3 shows a graph wherein each of the four samples were analyzed using a Waters ACQUITY UPLC-PDA-MS system. Major components were identified by mass, then verified through comparison to a prepared standard of the isolated molecule to confirm the identity. Major components of the extract are: arctigenin, cholorgenic acid, neocholorgenic acid, isochlorogenic acid A, arctiin, quercetin 3-O-β-D glucoside, cyanarin and casticin. Other components of the extract have not yet been identified. Sample collected from the extraction process was lyophilized to dryness and resuspended to a final concentration of 3.6 mg/mL in 0.1% formic acid (pH 4.2). Chromatography was achieved using a 20 μL injection volume and a Waters ACQUITY UPLC HSS T3, 100 Å, 2.1×100 mm, column. A gradient elution was used with Mobile Phase A of 0.1% formic acid (pH 4.2) and Mobile Phase B of 80:20 acetonitrile:water. The linear chromatographic gradient started with 95% Mobile Phase A and concluded with 5% Mobile Phase A over 19.1 minutes with a flow rate of 0.4 mL/min. Chromatograms were collected monitoring the column effluent at 236 nm with a UV/Vis detector and with a Single-Quadrapole (QDa) mass spectrometer set to monitor a mass range of 50-1200 Da. Samples were: EPE001 filtered at ~80° C. through an 11 μm qualitative filter (H3a), EPE001 filtered at ~80° C. through a 0.2 μm filter (H3b), EPE001 cooled to room temperature before filtration through an 11 μm qualitative filter (A3a), and EPE001 cooled to room temperature before filtration through a 0.2 μm filter (A3b).

V. Additional Examples

Figure 4:
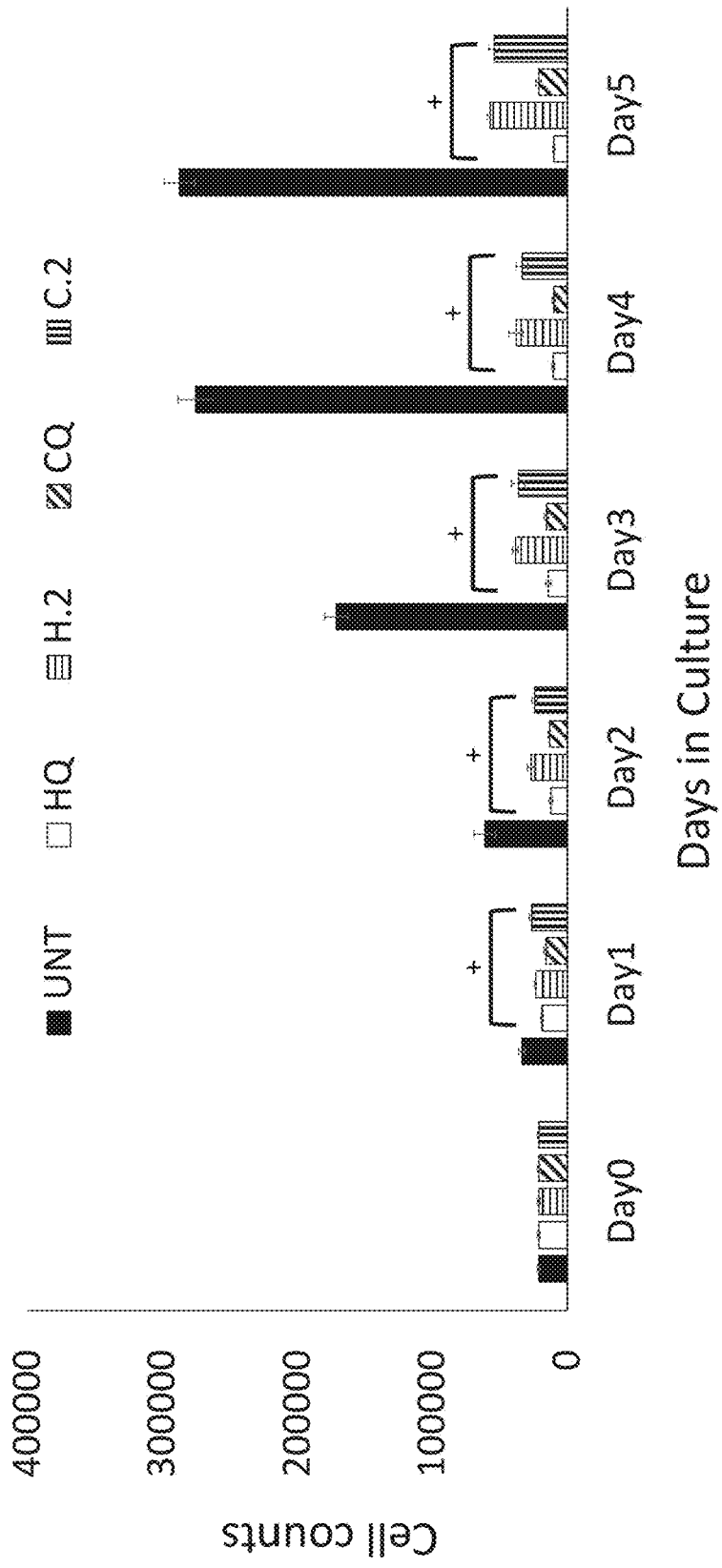
FIG. 4 is a bar graph depicting results of a treatment of human breast cancer cells utilizing a product produced by the process resulting from the embodiments of either FIG. 1 or FIG. 2.
Figure 5:
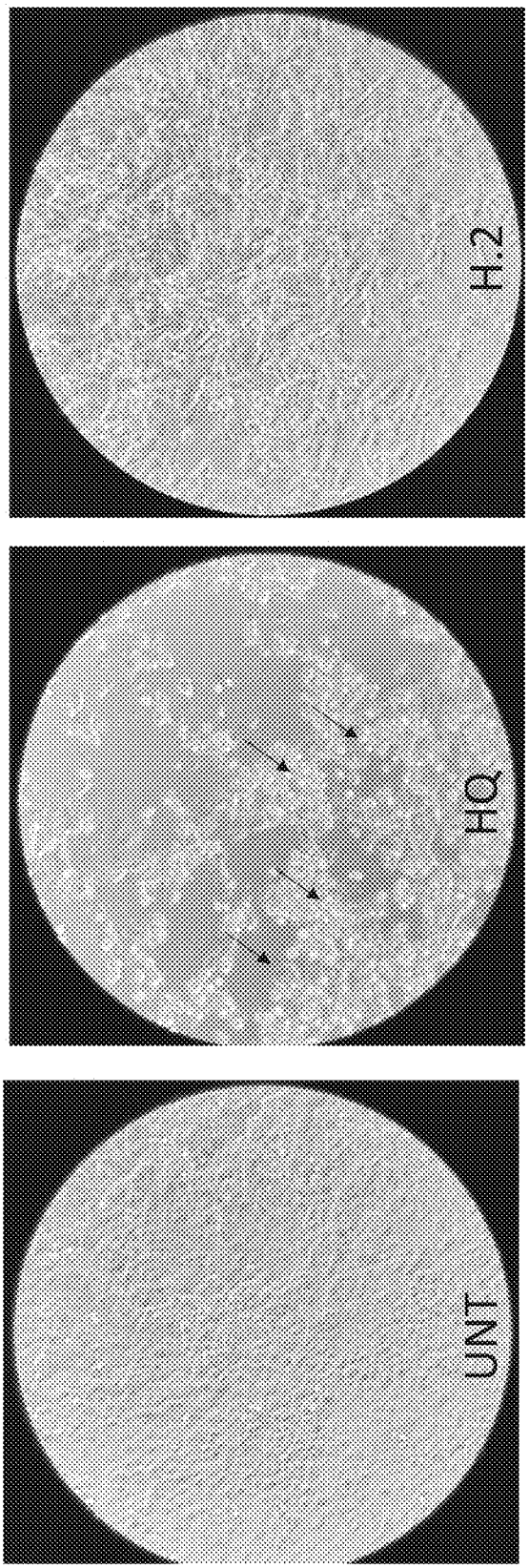
FIG. 5 shows a series of cells taken through a microscope on day 5 of the bar graph of FIG. 4.

FIGS. 4 and 5 are treatments of human breast cancer cells treated with an exemplary product of the extraction process (EPE001). 20,000 MCF7 (human breast adenocarcinoma) cells were seeded in 48 well plates in triplicate, allowed to adhere for 24 hours before treatment commenced (Day 0). Treatment groups were each performed in triplicate and include: untreated control group (UNT), treated with EPE001 filtered at ~80° C. through an 11 μm qualitative filter (HQ), treated with EPE001 filtered at ~80° C. through a 0.2 μm filter (H.2), treated with EPE001 cooled to room temperature before filtration through an 11 μm qualitative filter (CQ), and treated with EPE001 cooled to room temperature before filtration through a 0.2 μm filter (C.2). Cells were photographed and counted every 24 hours for 5 days. Images at Day 5 are represented in FIG. 5.

FIG. 4 shows the results in the form of a bar graph of applying each of the four filtered versions of EPE001 to MCF7 cells which are cultured human breast cancer cells. Control group samples that received no treatment (UNT) rose from 20,000 cells at day 0 to nearly 300,000 cells by the end of day 5. All applications of the example extract have a statistically significant (ANOVA p-value <0.05) impact on the growth of the cancer cells. By day 5, EPE001 filtered with the qualitative (11 μM) filter at 80° C. had the greatest cytotoxic effect, decreasing the original cell count by 28-fold in comparison to a 14× increase in cell count for the control group. Extract treated cancer cells not only showed strong cytotoxic effects, but also displayed an effect on the morphology of the cells as shown in FIG. 5. Treated cancer cells show changes in cell membrane permeability, diameter, volume and shape (rounder) as well as becoming less adherent to the microplate surface—suggesting multiple mechanisms of action resulting in cytotoxicity. Arrows indicate condensed cytoplasmic constituents, loss of membrane integrity and cell-cell as well as cell-substrate adhesion. When comparing the UNT cells to EPE001 treated samples, it is evident that there is significant cell loss. Furthermore, where the UNT cells look smooth and very confluent, cytoplasmic extension, stress and cell death features such as vacuolization and membrane blebbing.

Figure 6:
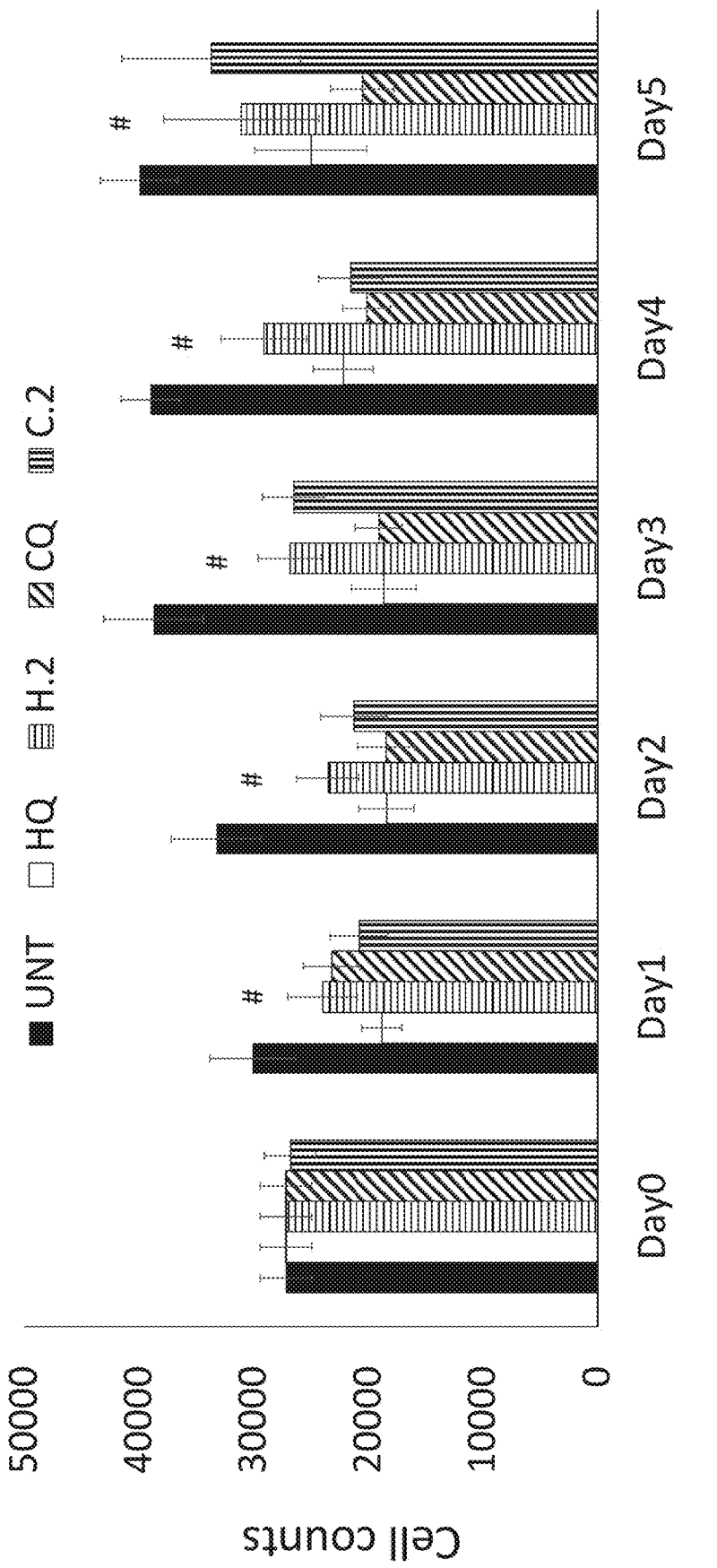
FIG. 6 is a bar graph depicting results of a treatment of human epithelial cells utilizing a product produced by the process resulting from the embodiments of either FIG. 1 or FIG. 2.
Figure 7:
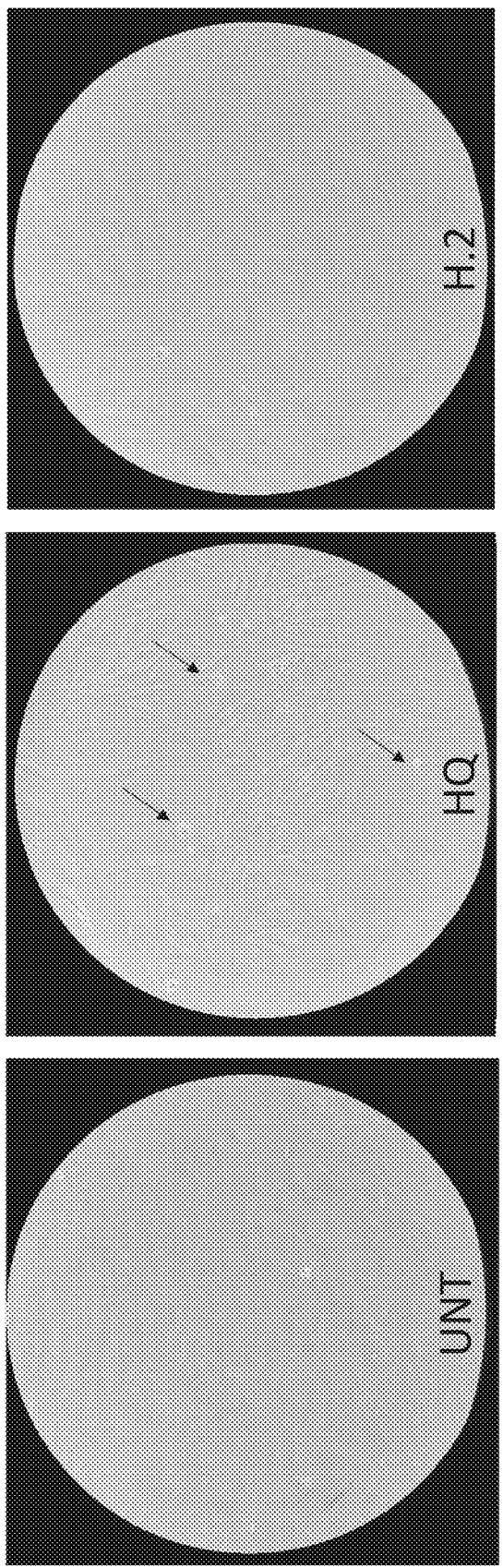
FIG. 7 shows a series of cells taken through a microscope on day 5 of the bar graph of FIG. 6.

Similarly, FIG. 6 and FIG. 7 are treatments of healthy human epithelial cells with an exemplary product of the extraction process (EPE001). 20,000 MCF10A (normal, human mammary epithelial) cells were seeded in 48 well plates in triplicate, allowed to adhere for 24 hours before treatment commenced (Day 0). Treatment groups were each performed in triplicate and include: untreated control group (UNT), treated with EPE001 filtered at ~80° C. through an 11 μm qualitative filter (HQ), treated with EPE001 filtered at ~80° C. through a 0.2 μm filter (H.2), treated with EPE001 cooled to room temperature before filtration through an 11 μm qualitative filter (CQ), and treated with EPE001 cooled to room temperature before filtration through a 0.2 μm filter (C.2). Cells were photographed and counted every 24 hours for 5 days. Images at Day 5 are represented in FIG. 7.

FIG. 6 shows the results in the form of a bar graph of applying each of the four filtered versions of EPE001 were applied to MCF10A cells which are cultured human normal epithelial breast cells. Control group samples that received no treatment rose from 20,000 cells at Day 0 to ~40,000 cells by the end of day 5. It should be noted that normal mammary epithelial cells grow more slowly and are constrained by area and cell-cell interactions whereas cancer cells grow much faster and are not constrained either by confluence or cell-cell boundaries. EPE001 filtered with the 0.2 μm filter at 80° C. did not have a statistically significant change in cell count by the end of day 5 (ANOVA p-value >0.05, meaning there is no statistical significance in the comparison).

Figure 8:
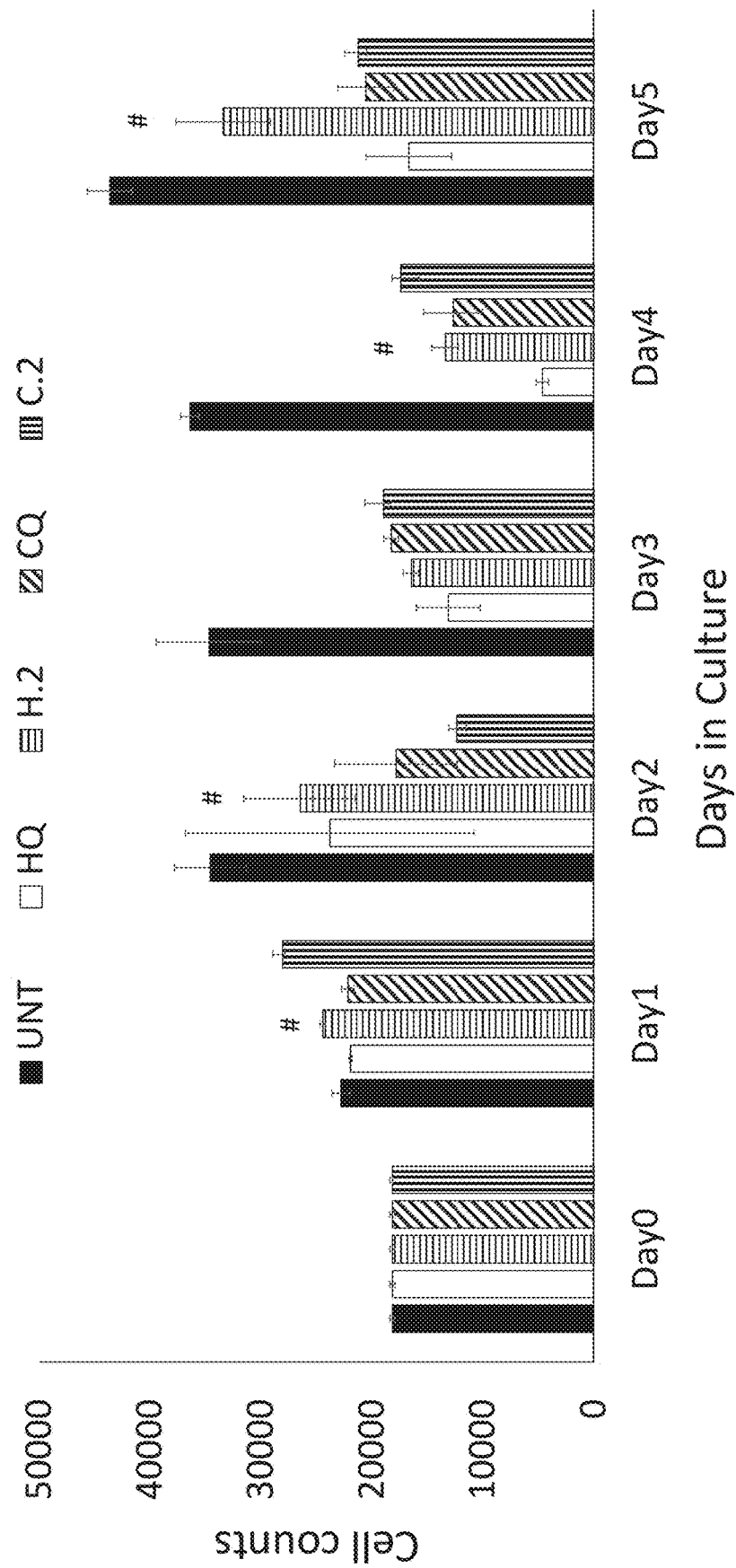
FIG. 8 is a bar graph depicting results of a treatment of fibroblast cells utilizing a product produced by the process resulting from the embodiments of either FIG. 1 or FIG. 2.

Cells treated with the 0.2 μm filtered EPE001 did not show morphological differences, as shown in FIG. 7, from untreated cells. Cells treated with the qualitative filter (11 μM) EPE001 did show slight morphological differences with some cytotoxicity. Additionally, cells treated with EPE001 became more adherent to the walls of the microplate, which may account for some of the cell count differences between treated cells and the untreated control samples. Given that epithelial cells serve as barriers for the body, this adherent property was considered beneficial FIG. 8 shows the results in the form of a bar graph of applying each of the four filtered versions of EPE001 were applied to HFF1 cells which are cultured human normal foreskin fibroblast cells. Control group samples that received no treatment proliferated from 20,000 cells at day 0 to ~45,000 cells by the end of day 5. It should be noted that normal fibroblast cells grow more slowly and are constrained by area and cell-cell interactions whereas cancer cells grow much faster and are not constrained either by confluence or cell-cell boundaries. EPE001 filtered with the 0.2 μm filter at 80° C. did not have a statistically significant change in cell count by the end of day 5 (ANOVA p-value >0.05, meaning there is no statistical significance in the comparison).

Figure 9:
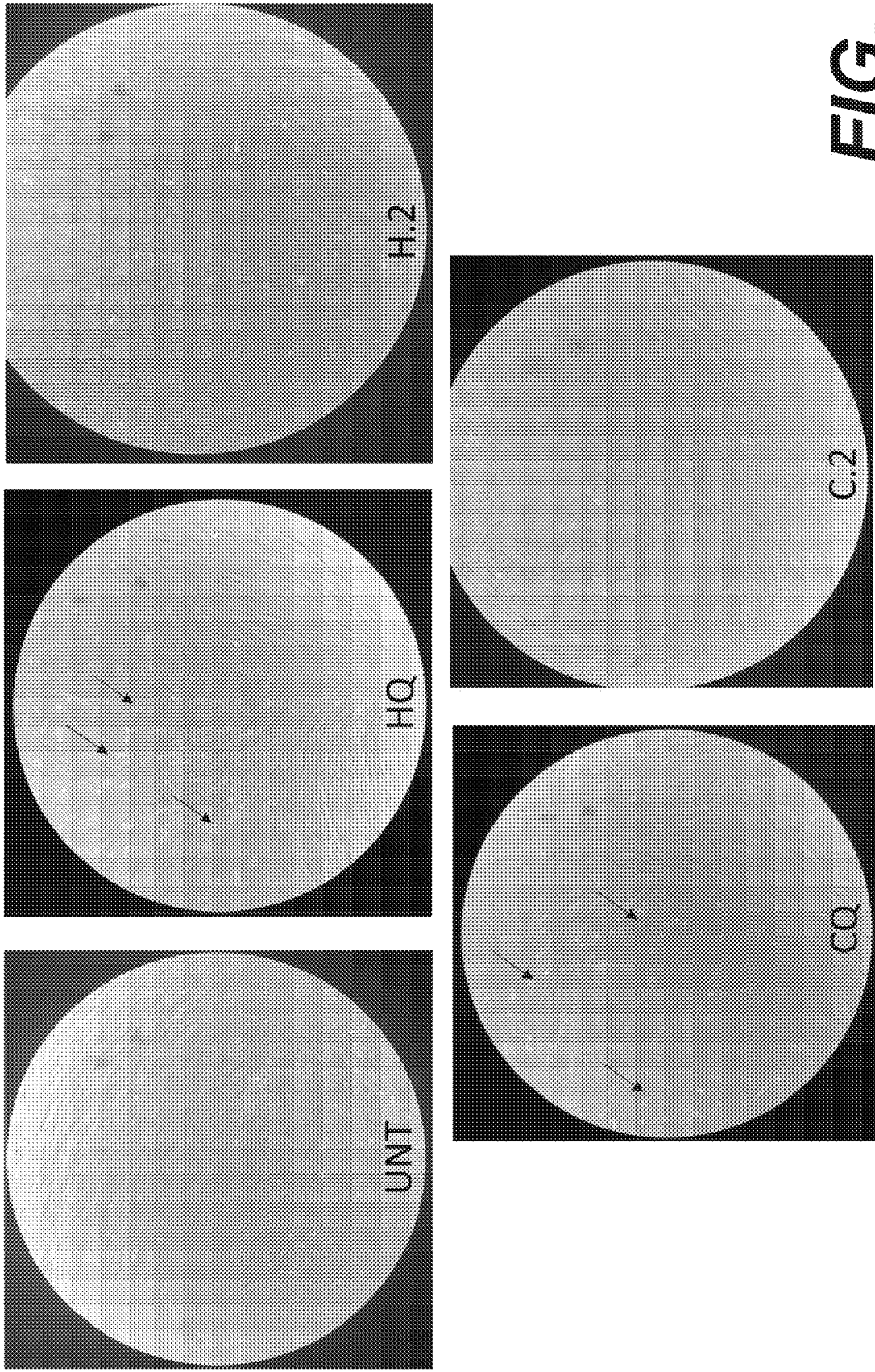
FIG. 9 shows a series of cells taken through a microscope on day 5 of the bar graph of FIG. 8.

Cells treated with EPE001 filtered with the 0.2 μm filter at 80° C. did not show morphological differences in comparison to the untreated control group as shown in FIG. 9. However, the other filtration versions of EPE001 showed loss of cells, increased cell size and more strongly delineated boundaries. As with the epithelial cells, fibroblast cells treated with EPE001 became more adherent to the walls of the microplate, which may account for some of the cell count differences between treated cells and the untreated control samples. In this case, stronger adherence is positive attribute, especially since fibroblast cells comprise the structural framework of connective tissues and play key roles in wound healing.

VI. RNA-Seq Analysis of Changes in Gene Regulation Due to Extract

RNA-Seq analysis or Whole Transcriptome Shotgun Sequencing (WTSS) uses a Next-Generation Sequencing (NGS) method to catalog and count the number of RNA transcripts produced in a selected cell culture. This technique can be used as a comparative tool to determine which genes are activated or suppressed and to what degree in different environments—in this example, with and without the presence of the Extract Product. Data collected from RNA-Seq analysis is analyzed utilizing a web-based software application, Ingenuity Pathway Analysis (IPA), produced by QIAGEN Bioinformatics.

FIG. 10 is a summary of gene expression changes in the presence of an exemplary product of the extraction process (EPE001) using RNA-Seq analysis. MCF7 (human breast adenocarcinoma) cells were seeded at $1 \times 10^{\wedge}6$ cells in T25 flasks and incubated at 37° C., 5% $CO_2$ for 24 hours. Cells were allowed to adhere for 24 hours before treatment commenced. Cells were treated with medium only (reference sample) or treated with EPE001 and allowed to incubate for 24 hours. Cells were harvested and RNA was isolated using a Qiagen RNeasy Mini Kit as per manufacturer instruction. RNA transcriptome was sequenced using an Illumina MiSeq system. FASTQ files were generated by the Illumina CASAVA v1.8.2 and the quality of reads was evaluated by NGSQC Toolkit v2.3. High-quality reads were mapped, annotated to exons, and normalized to FPKM values for all 25,278 human RNA references in NCBI RefSeq database. Differential gene expression analysis was determined using DNAstar software. Biological pathway analyses were carried out using Ingenuity Pathway Analysis (Qiagen).

For this example, untreated MCF7 breast cancer cells were used as a control. The differences between this control and the MCF7 breast cancer cells treated with EPE001 (filtered at 80° C. with a 0.2 μm filter) using RNA-Seq analysis. The table shown in FIG. 10 represents the IPA software output of genes upregulated (increase in the physical number of RNA transcripts produced for a particular gene) or downregulated (decrease in the physical number of RNA transcripts produced for a particular gene) in the presence of the Extract Product.

The gene, HGF (hepatocyte growth factor), is involved in cell growth and has higher expression in cancer cells. This gene is downregulated in the presence of EPE001.

The gene, VEGF (vascular endothelial growth factor), has been implicated in promoting blood supply to cancer cells and the metastatic cascade. This gene is downregulated in the presence of EPE001.

The gene, HSPG2 (heparan sulfate proteoglycan 2), is involved in angiogenesis, β-amyloid binding, abnormal morphology and cell proliferation. This gene is also downregulated in the presence of EPE001.

The gene, TP53 (tumor protein 53), is a well-studied tumor suppressor gene that is involved in regulation of cell death and prevention of proliferation. This gene is upregulated in the presence of EPE001.

The gene, NUPR1 (nuclear protein 1), regulates cell death and signals TP53, which is a tumor suppressor gene. This gene is upregulated in the presence of EPE001.

In summary, important upstream regulator genes associated with cancer proliferation are downregulated in the presence of the Extract Product. Important upstream master tumor suppressor genes are upregulated in the presence of EPE001. The RNA-Seq analysis coincides with the physical results seen in FIGS. 4 and 5.

Figure 11:
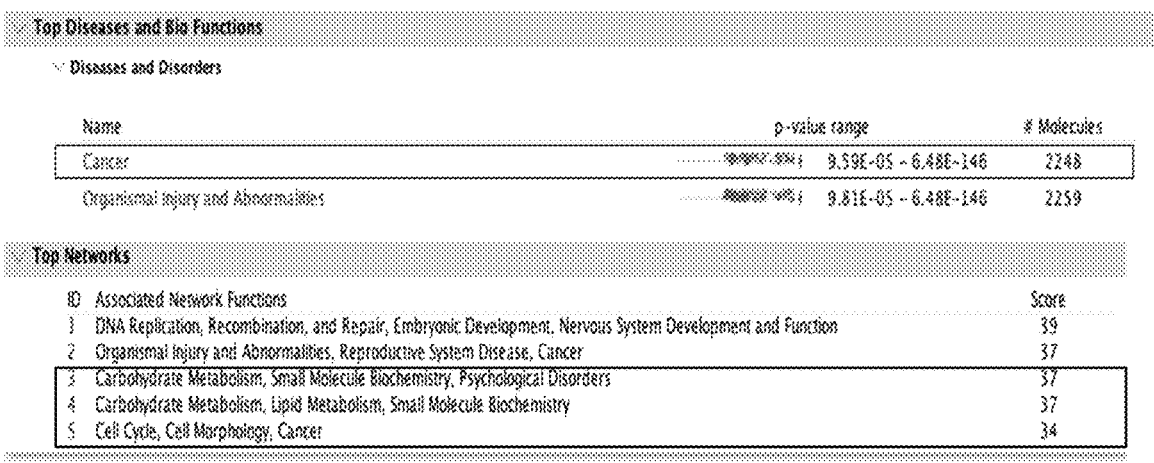
FIG. 11 is a table including a summary of diseases and associated networks that are affected as a result in upregulation or downregulation of the summary from the RNA-Seq analysis.

FIG. 11 is a summary of diseases and associated networks that are affected as a result in upregulation or downregulation of the summary from the RNA-Seq analysis. This output represents the top scoring diseases and networks as determined by the Ingenuity Pathway Analysis (Qiagen) software package.

Additionally, treatment of cancer cells with EPE001 resulted in over 2000 molecules that were upregulated or downregulated, many of which are involved in tumor suppression and inhibition of cell growth. Outside of cancer related networks, EPE001 also had an effect on genes associated with DNA replication, recombination and repair, embryonic development, nervous system development and function. These results would suggest an increase in stimulation of healing, stem cell activity, as well as stimulation of hair growth.

There was also an upregulation in genes associated with lipid metabolism which would suggest EPE001 would increase lipid metabolism. This has negative effects on cancer cells because they rely on carbohydrate metabolism for proliferation. This phenomenon also suggests that energy output would increase in healthy cells when using lipid substrates rather than carbohydrates because the process of ß-oxidation yields ~4× as much energy as aerobic respiration (glucose-dependent).

It is to be understood that while certain embodiments and/or aspects of the invention have been shown and described, the invention is not limited therein and encompasses various other embodiments and aspects.

Having thus described the invention, what is claimed as new and desired to be secured by Letters Patent is:

1. An aqueous extraction system comprising:
   an extraction vessel configured to store a fibrous container and a volume of water;
   a heating element configured to heat said volume of water within said extraction vessel, thereby creating water vapor and heated water;
   an active ingredient mixture consisting of: *Cinnamomum cassia, Arctium lappa, Vitex agnus castus, Lonicera japonica, Acanthopanax gracilistylis, Raphanus sativus, Astragalus membranaceus* and *Hordeum vulgare* and configured to be a dry mixture placed within said fibrous container;
   said heated water configured to draw volatiles and said extraction mixture from said dry mixture;
   a condenser connected to said extraction vessel, said condenser configured to remove water vapor and volatiles; and
   said extraction mixture configured to be used as a treatment.

2. The system of claim 1, further comprising:
   a purified water reservoir and a first pump, said first pump configured to draw said volume of water from said purified water reservoir into said extraction vessel; and
   at least one valve, at least one second pump, and at least one filter aligned in a series and configured to draw said extraction mixture from said extraction vessel into one or more storage containers.

3. The system of claim 1,
   wherein said active ingredient mixture comprises: 220 mg of *Cinnamomum cassia,* 110 mg *Arctium lappa,* 220 mg *Vitex agnus castus,* 110 mg *Lonicera japonica,* 110 mg *Acanthopanax* gracilistylis, 110 mg *Raphanus sativus,* 110 mg *Astragalus membranaceus* and 220 mg *Hordeum vulgare* for each liter of said volume of water; and
   wherein said extraction mixture is filtered in succession via simple vacuum assisted filtration using membrane filters having a pore size smaller than one micron.

4. The system of claim 3, wherein said extraction mixture being filtered a first time at a temperature between 90°-100° Celsius.

5. The system of claim 4, wherein said extraction mixture being filtered a second time at a temperature between 70°-85° Celsius.

6. The system of claim 5, wherein said extraction mixture being filtered a third time at a temperature between 40°-60° Celsius.

7. The system of claim 6, wherein said extraction mixture being filtered a fourth time at a temperature between 15°-30° Celsius.

8. The system of claim 7, wherein said extraction mixture being filtered a fifth time at a temperature between 5°-15° Celsius, such that said extraction mixture contains approximately 370 mg of biologically active solid ingredients per liter of extraction mixture.

9. A method of producing an aqueous extract, the method comprising the steps:
   a) placing a dry mixture within a fibrous container, said dry mixture consisting of: *Cinnamomum cassia, Arctium lappa, Vitex agnus castus, Lonicera japonica, Acanthopanax gracilistylis, Raphanus sativus, Astragalus membranaceus* and *Hordeum vulgare;*
   b) placing said fibrous container within an extraction vessel;
   c) filling said extraction vessel with a volume of water;
   d) heating said volume of water with a heating element about said extraction vessel such that draw volatiles, water vapor, and an extraction mixture are generated from said dry mixture within said volume of water;
   e) removing said water vapor with a condensing unit connected to said extraction vessel;
   f) filtering said extraction mixture out of said extraction vessel.

10. The method of claim 9, further comprising the step:
    mixing 220 mg of *Cinnamomum cassia,* 110 mg *Arctium lappa,* 220 mg *Vitex agnus castus,* 110 mg *Lonicera japonica,* 110 mg *Acanthopanax* gracilistylis, 110 mg *Raphanus sativus,* 110 mg *Astragalus membranaceus* and 220 mg *Hordeum vulgare* for each liter of said volume of water to create said dry mixture.

11. The method of claim 10, further comprising the step: filtering said extraction mixture in succession via simple vacuum assisted filtration using membrane filters having a pore size smaller than one micron a first time at a temperature between 90°-100° Celsius.

12. The method of claim 11, further comprising the step: filtering said extraction mixture a second time at a temperature between 70°-85° Celsius.

13. The method of claim 11, further comprising the step: filtering said extraction mixture a second time at a temperature between 40-60 Celsius.

14. The method of claim 11, further comprising the step: filtering said extraction mixture a second time at a temperature between 15-30 Celsius.

15. The method of claim 11, further comprising the step: filtering said extraction mixture a second time at a temperature between 5-15 Celsius.

* * * * *